United States Patent [19]

Diamond

[11] 4,115,447
[45] Sep. 19, 1978

[54] CARBAMYLGUANIDINE ANTIMICROBIAL COMPOUNDS

[75] Inventor: Julius Diamond, Morris Plains, N.J.

[73] Assignee: Cooper Laboratories, Inc., Parsippany, N.J.

[21] Appl. No.: 757,577

[22] Filed: Jan. 7, 1977

Related U.S. Application Data

[62] Division of Ser. No. 546,549, Feb. 3, 1975, Pat. No. 4,022,962.

[51] Int. Cl.$^2$ .................. C07C 127/15; A61K 31/17
[52] U.S. Cl. .............................................. 260/553 R
[58] Field of Search .......... 260/553 R, 553 A, 501.14, 260/345.7; 536/18, 1

[56] References Cited

U.S. PATENT DOCUMENTS

| | | | |
|---|---|---|---|
| 3,564,041 | 2/1971 | Farrissey et al. | 260/553 R |
| 3,798,269 | 3/1974 | Cutler | 260/553 R |
| 4,022,834 | 5/1977 | Gundersen | 260/501.14 |

*Primary Examiner*—James O. Thomas, Jr.
*Assistant Examiner*—G. T. Breitenstein
*Attorney, Agent, or Firm*—John J. Kolano; Thomas R. Boland

[57] ABSTRACT

Antimicrobial compounds are disclosed having the formula:

Z—B—Y—B—Z · nHA wherein B is carbamylguanidino, or thiocarbamylguanidino, Y is a bivalent organic radical selected from the group consisting of $C_2$-$C_{12}$ alkylene, $C_5$-$C_{12}$ cycloalkylene, $C_5$-$C_{12}$ cycloalkylenebis(loweralkyl), $C_6$-$C_{12}$ arylene and loweralkylarylene, $C_7$-$C_{12}$ aryleneloweralkyl, and $C_8$-$C_{12}$ arylenebis(loweralkyl) and Z is selected from the group consisting of $C_1$-$C_{12}$ alkyl; $C_4$-$C_{12}$ dialkylaminoalkyl; $C_3$-$C_{12}$ alkenyl; $C_3$-$C_{12}$ alkynyl; $C_3$-$C_{12}$ cycloalkyl, $C_4$-$C_{12}$ cycloalkylalkyl; $C_1$-$C_{10}$ alkoxy $C_{10}$-$C_2$ alkyl having a total carbon content of $C_3$-$C_{14}$; $C_1$-$C_{10}$ alkylthio $C_{10}$-$C_2$ alkyl having a total carbon content of $C_3$-$C_{14}$; phenoxy $C_2$-$C_6$ alkyl; phenylthio $C_2$-$C_6$ alkyl; $C_6$-$C_{14}$ aryl; $C_7$-$C_{14}$ aralkyl; and arylcycloalkyl; and $C_6$-$C_{14}$ aryl and aralkyl substituted with one or more radicals selected from the group consisting of loweralkyl, trifluoromethyl, loweralkoxy, trifluoromethoxy, phenoxy, loweralkylthio, halo, nitro, cyano, $C_2$-$C_6$ acyl, benzoyl, alkoxycarbonyl, diloweralkylamino, loweralkylsulfonyl, fluorosulfonyl and alkylsulfinyl; $n = 0, \frac{1}{3}, \frac{1}{2}, \frac{2}{3}, 1, 2$ and HA is an inorganic or organic acid.

14 Claims, No Drawings

CARBAMYLGUANIDINE ANTIMICROBIAL COMPOUNDS

RELATED APPLICATIONS

This application is a division of Assignee's copending application Ser. No. 546,549, filed Feb. 3, 1975 now U.S. Pat. No. 4,022,962.

BACKGROUND OF THE INVENTION

This invention relates to novel compounds which are useful as topical antimicrobial agents and more particularly to antimicrobial compounds which are adsorbed to teeth, and which are effective against the microorganisms that produce dental plaque.

Dental plaque is a soft, tenacious bacterial deposit which forms on the surface of the teeth. It is produced by the action of certain bacteria viz., *S. mutans, A. viscosus,* and *A. naeslundi,* on carbohydrate substances in the mouth. Of the numerous antimicrobial agents that have been investigated for their ability to inhibit plaque formation, only 1,6-bis-(p-chlorophenylbiguanidino)-hexane (chlorhexidine) and 1,6-bis-(2-ethylhexylbiguanidino)hexane (alexidine) are reported to be clinically effective antiplaque agents. However, because these agents are extremely strong organic bases, and consequently are almost entirely cationic at the prevailing pH of the mouth, they suffer from the following disadvantages: (1) they are preferentially adsorbed to the oral mucosa rather than to the teeth, (2) they are extremely bitter-tasting substances, (3) they produce local irritation of the oral mucosa and tongue, (4) when swallowed they are adsorbed to the gastrointestinal mucosa.

SUMMARY OF THE INVENTION

It is accordingly the objective of this invention to provide novel compounds which are useful as topical antimicrobial agents. A further objective is to provide novel antimicrobial compounds which adsorb to teeth and which are inhibitors of plaque-producing bacteria, which are essentially atoxic to mammals by oral administration, and which are essentially tasteless.

It has now been found that the objectives of this invention can be attained by providing antimicrobial compounds related to the bis-biguanides, but in which one or both of the strongly basic biguanide functions has been replaced by the weaker basic functions carbamylguanidino, or thiocarbamylguanidino. The objectives of this invention have been attained by using novel compounds of the formula:

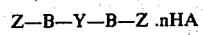

wherein B is carbamylguanidino, or thiocarbamylguanidino, Y is a bivalent organic radical selected from the group consisting of $C_2$-$C_{12}$ alkylene, $C_5$-$C_{12}$ cycloalkylene, $C_5$-$C_{12}$ cycloalkylenebis(loweralkyl), $C_6$-$C_{12}$ arylene and loweralkylarylene, $C_7$-$C_{12}$ aryleneloweralkyl, and $C_8$-$C_{12}$ arylenebis(loweralkyl) and Z is selected from the group consisting of $C_1$-$C_{12}$ alkyl; $C_4$-$C_{12}$ dialkylaminoalkyl; $C_3$-$C_{12}$ alkenyl; $C_3$-$C_{12}$ alkynyl; $C_3$-$C_{12}$ cycloalkyl, $C_4$-$C_{12}$ cycloalkylalkyl; $C_1$-$C_{10}$ alkoxy $C_{10}$-$C_2$ alkyl having a total carbon content of $C_3$-$C_{14}$; $C_1$-$C_{10}$ alkylthio $C_{10}$-$C_2$ alkyl having a total carbon content of $C_3$-$C_{14}$; phenoxy $C_2$-$C_6$ alkyl; phenylthio $C_2$-$C_6$ alkyl; $C_6$-$C_{14}$ aryl; $C_7$-$C_{14}$ aralkyl and arylcycloalkyl; and $C_6$-$C_{14}$ aryl and aralkyl substituted with one or more radicals selected from the group consisting of loweralkyl, trifluoromethyl, loweralkoxy, trifluoromethoxy, phenoxy, loweralkylthio, halo, nitro, cyano, $C_2$-$C_6$ acyl, benzoyl, alkoxycarbonyl, diloweralkylamino, loweralkylsulfonyl, fluorosulfonyl and alkylsulfinyl; and pharmacologically acceptable addition salts of these compounds with acids represented by nHA in which $n = 0, \frac{1}{4}, \frac{1}{2}, \frac{3}{4}, 1, 2$ and HA is an inorganic or organic acid. Lower alkyl denotes an alkyl group containing 1–6 carbon atoms.

The term "carbamylguanidino" includes both unsubstituted and loweralkyl-substituted groups having the formula:

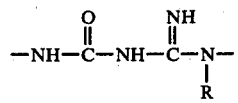

wherein R may be hydrogen or loweralkyl. Likewise, the biguanidino group may be alkyl substituted, having the formula:

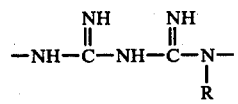

wherein R is as defined above.

The central group Y may be connected to the substituted guanidino groups B either through the guanidino portion of the group or through the carbamyl or thiocarbamyl portion. Thus the invention includes compounds of the following structures:

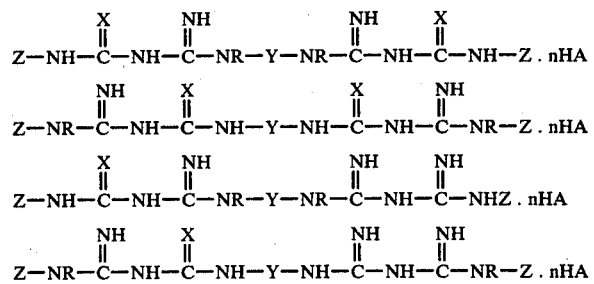

wherein X represents O or S and the other symbols are as defined above.

The compounds of this invention, while related to the bis-biguanides, are considerably weaker bases as a consequence of replacing one or both of the biguanidino functions by a carbamylguanidino or thiocarbamylguanidino function. The carbamylguanidino compounds of this invention, while retaining the desirable antimicrobial activity of the bis-biguanide compounds, provide useful improvements over the latter substances. The carbamylguanidino compounds of this invention bind to teeth, and are essentially tasteless and atoxic to mammals by oral administration. Because the carbamylguanidino compounds are weaker bases than the bis-biguanidino compounds, the former compounds can serve as excellent ligands in their non-cationic form to chelate with calcium. Consequently the carbamylguanidino compounds of this invention are able to bind to dental hydroxyapatite through chelation with the surface calcium ions of the hydroxapatite crystal lattice of teeth. The bis-biguanidino compounds which are almost entirely in their cationic form at physiological pH's are incapable of serving as good ligands with calcium ions.

DESCRIPTION OF THE PREFERRED EMBODIMENTS

In the Y portion of the novel compounds of this invention, the aliphatic groups may be straight chain or branched. Suitable groups for the Y portion include the following: $C_2$–$C_{12}$ alkylene, e.g., ethylene, trimethylene, tetramethylene, pentamethylene, hexamethylene, heptamethylene, octamethylene, nonamethylene, decamethylene, undecamethylene, dodecamethylene, methylethylene, 1,3-butylene, 2,3-butylene, 1,3-neopentylene, 2,5-dimethyl-2,5-hexylene; $C_4$–$C_{12}$ alkenylene, e.g., 2-buten-1,4-diyl, $C_4$–$C_{12}$ alkynylene, e.g., 2-butyne-1,4-diyl, $C_5$–$C_{12}$ cycloalkylene, e.g., 1,2-cyclopentylene, 1,2-cyclohexylene, 1,3-cyclohexylene, 1,4-cyclohexylene, 1,6-cyclodecylene, 1,2-cycloheptylene, 1,2-cyclooctylene; $C_5$–$C_{12}$ cycloalkylene bis(loweralkyl), e.g., 1,4-cyclohexylenedimethyl, 1,2-cyclopentylenedimethyl, 1,2-cyclobutylenedimethyl, 1,1-cyclopropylenedimethyl, 1,3-cyclopentylenedimethyl, 1,3-cyclopentylenedipropyl; $C_6$–$C_{12}$ arylene, e.g., 1,2-phenylene, 1,3-phenylene, 1,4-phenylene, 2,5-tolylene, 2,4-tolylene, 2,6-tolylene, 3,4-tolylene, 2,5-p-xylylene, 2,5-o-xylylene, 4,4'-p-biphenylene, 1,2-naphthylene, 1,5-naphthylene, 1,8-naphthylene, 2,3-naphthylene, 2,6-naphthylene, 2,7-naphthylene, $C_7$–$C_{12}$ aryleneloweralkyl, e.g., o-tolylene, m-tolylene; $C_8$–$C_{12}$ arylenebis(loweralkyl), e.g., α,α'-m-xylylene.

Among these groups the preferred groups are $C_4$–$C_8$ alkylene, straight chain and branched, $C_5$–$C_8$ cycloalkylene, $C_5$–$C_8$ cycloalkylenebis(loweralkyl) and loweralkylarylene, $C_7$–$C_8$ phenyleneloweralkyl and $C_8$ phenylenebis(loweralkyl). More preferred as group Y are pentamethylene, hexamethylene, heptamethylene, 1,4-cyclohexylenedimethyl, and α,α'-m-xylylene radicals.

Preferred for group B are carbamylguanidino groups, and the preferred compounds containing these groups are those in which the guanidino portion of the group is bonded to the central group Y. Thus the preferred compounds are those having the formula:

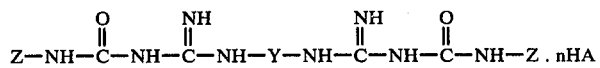

Suitable groups for Z in the novel compounds include: $C_1$–$C_{12}$ alkyl, e.g., methyl, ethyl, 1-propyl, 1-butyl, 1-pentyl, 1-hexyl, 1-heptyl, 1-octyl, 1-nonyl, 1-decyl, 1-undecyl, 1-dodecyl, 2-propyl, i-butyl, t-butyl, 2-pentyl, i-pentyl, neopentyl, 1-methylpentyl, 2-methylpentyl, 3-methylpentyl, 4-methylpentyl, 2-ethylbutyl, 1-methylhexyl, 2-ethylhexyl, 2-methylheptyl, 1,5-dimethylhexyl, 1,3-dimethylpentyl, 1,4-dimethylpentyl, $C_4$–$C_{12}$ dialkylaminoalkyl, e.g., diethylaminoethyl, 2(N-piperidino)ethyl, 2-(N-morpholino)ethyl; $C_3$–$C_{12}$ alkenyl, e.g., allyl, 10-undecenyl, 2-ethyl-2-hexen-1-yl, 2,4-dimethyl-2-penten-3-yl, 9-decenyl, 5-hexen-3-yl; $C_3$–$C_{12}$ alkynyl, e.g., propargyl, 2-butynyl, 2-pentynyl, 2-dodecynyl, 3-butynyl, 4-ethyl-1-hexyn-3-yl; $C_3$–$C_{12}$ cycloalkyl, e.g., cyclopropyl, cyclobutyl, cyclopentyl, 2-methylcyclopentyl, 3-methylcyclopentyl, cyclohexyl, 2-methylcyclohexyl, 3-methylcyclohexyl, 4-methylcyclohexyl, 2-isopropyl-5-methylcyclohexyl, 3-isopropyl-6-methylcyclohexyl, cycloheptyl, cyclooctyl, cyclononyl, adamantyl, cyclodecyl, cyclododecyl; $C_4$–$C_{12}$ cycloalkylalkyl, e.g., cyclopropylmethyl, cyclobutylmethyl, cyclopentylmethyl, cyclohexylmethyl, cycloheptylmethyl, 1-cyclohexylethyl, 2-cyclohexylpropyl, cyclooctylmethyl; $C_1$–$C_{10}$ alkoxy $C_{10}$–$C_2$ alkyl, e.g., 2-ethoxyethyl, 2-butoxyethyl, 2-hexoxyethyl, 3-hexoxypropyl, $C_1$–$C_{10}$ alkylthio $C_{10}$–$C_2$ alkyl, e.g., 2-ethylthioethyl, 2-butylthioethyl; aryloxy $C_2$–$C_6$ alkyl, e.g., 2-phenoxyethyl, 4-phenoxybutyl; phenylthio $C_2$–$C_6$ alkyl, e.g., 2-phenylthioethyl; $C_6$–$C_{14}$ aryl, e.g., phenyl, 4-biphenylyl, 1-naphthyl, 5,6,7,8-tetrahydro-1-naphthyl; $C_7$–$C_{14}$ aralkyl, e.g., benzyl, 1-phenylethyl, 2-phenylethyl, $C_9$–$C_{14}$ arylcycloalkyl, e.g., 2-phenylcyclopropyl; $C_6$–$C_{14}$ aryl and aralkyl substituted with groups such as: loweralkyl, e.g., 2-tolyl, 3-tolyl, 4-tolyl, 2-isopropylphenyl, 4-isopropylphenyl, 4-butylphenyl, 4-hexylphenyl, 2,4-dimethylphenyl, 2,6-dimethylphenyl, 3,5-dimethylphenyl, 2,6-diethylphenyl, 2,6-diisopropylphenyl, 2-ethyl-6-methylphenyl, 2-methyl-6-isopropylphenyl, 2,4,5-trimethylphenyl, 2,4,6-trimethylphenyl, 2-methylbenzyl, 3-methylbenzyl, 4-methylbenzyl; trifluoromethyl, e.g., 2-trifluoromethylphenyl, 3-trifluoromethylphenyl, 4-trifluoromethylphenyl, 3,5-bis(trifluoromethyl)phenyl, 2-trifluoromethylbenzyl, 3-trifluoromethylbenzyl, 4-trifluoromethylbenzyl; loweralkoxy, e.g., 2-methoxyphenyl, 4-methoxyphenyl, 4-ethoxyphenyl, 4-butoxyphenyl, 2,4-dimethoxyphenyl; trifluoromethoxy aryl, e.g., 4-trifluoromethoxyphenyl; phenoxy, e.g., 4-phenoxyphenyl; loweralkylthio, e.g., 3-methylthiophenyl, 4-methylthiophenyl, 4-ethylthiophenyl; halo, e.g., 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 4-iodophenyl, 4-chloro-1-naphthyl, 2,3-dichlorophenyl, 2,4-dichlorophenyl, 2,6-dichlorophenyl, 3,5-dichlorophenyl, 3,4-dichlorophenyl, 2,4-dibromophenyl, 2,5-difluorophenyl, 2,4,5-trichlorophenyl, 2,4,6-trichlorophenyl, 2,3,4,5-tetrachlorophenyl, 2,3,4,5,6-pentafluorophenyl, 2-chlorobenzyl, 3-chlorobenzyl, 4-chlorobenzyl, 4-fluorobenzyl, 4-bromobenzyl, 2-(4-chlorophenyl)ethyl; nitro, e.g., 2-nitrophenyl, 3-nitrophenyl, 4-nitrophenyl, 4-nitrobenzyl; cyano, e.g., 2-cyanophenyl, 3-cyanophenyl, 4-cyanophenyl; acyl, e.g., 2-acetylphenyl, 3-acetylphenyl, 4-acetylphenyl, 4-acetylbenzyl; benzoyl, e.g., 4-benzoylphenyl; loweralkoxycarbonyl, e.g., 2-ethoxycarbonyl, 3-ethoxycarbonyl, 4-ethoxycarbonyl; diloweralkylamino, e.g., 3-dimethylaminophenyl, 4-dimethylaminophenyl, 4-dimethylaminophenyl; loweralkylsulfonyl, e.g., 4-butylsulfonylphenyl, 4-methylsulfonylphenyl; fluorosulfonyl, e.g., 3-fluorosulfonylphenyl; loweralkylsulfinyl, e.g., 3-methylsulfinylphenyl, 4-methylsulfinylphenyl; mixed substituents, e.g., 4-bromo-2,6-dimethylphenyl, 2-chloro-6-methylphenyl, 5-chloro-2-methylphenyl, 2-chloro-5-trifluoromethylphenyl, 4-chloro-3-trifluoromethylphenyl, 2-chloro-4-nitrophenyl, 2-chloro-4-nitrophenyl, 2-chloro-5-nitrophenyl, 4-chloro-2-nitrophenyl, 2-methoxy-5-methylphenyl, 2-methoxy-4-nitrophenyl, 2-methoxy-5-nitrophenyl, 4-methyl-2-nitrophenyl, 4-methyl-3-nitrophenyl, 3-chloro-4-fluorophenyl, 3-chloro-2-methoxyphenyl, 4-chloro-2-methoxyphenyl, 2-fluoro-3-nitrophenyl, 2-fluoro-5-nitrophenyl, 3-chloro-2-phenoxyphenyl, 3-chloro-2,4-dimethoxyphenyl, 4,5-dimethyl-2-nitrophenyl, 4-methylthio-3-chlorophenyl;

Phenyl groups substituted with hydroxyl, carboxyl, carboxamido, N-loweralkylcarboxamido, N,N-diloweralkylcarboxamido, amino, loweralkylamino, amido, loweracyloxy, mercapto, sulfonic acid, sulfonyl chloride, sulfonamido, loweralkylsulfonamido, and diloweralkylsulfonamido groups can also be used as Z.

Among these groups the preferred Z groups are $C_4$–$C_{10}$ alkyl, straight chain and branched, $C_5$–$C_9$ cycloalkyl, $C_6$–$C_9$ cycloalkylalkyl, phenyl, naphthyl, phenyl $C_1$–$C_4$ alkyl, phenyl $C_3$ cycloalkyl, $C_1$–$C_4$ alkylphenyl, $C_1$–$C_3$ alkylbenzyl, trifluoromethylphenyl, trifluoromethylbenzyl, $C_1$–$C_4$ alkoxyphenyl, trifluoromethoxyphenyl, phenoxyphenyl, $C_1$–$C_4$ alkylthiophenyl, halophenyl, halobenzyl, $C_1$–$C_4$ acylphenyl, $C_1$–$C_4$ alkoxycarbonylphenyl, $C_1$–$C_4$ alkylsulfonylphenyl and $C_1$–$C_4$ fluorosulfonylphenyl. More preferred groups are 2-ethylhexyl, 1,5-dimethylhexyl, 1,3-dimethylpentyl, 1,4-dimethylpentyl, cyclohexylmethyl, phenyl, 4-tolyl, 1-phenylethyl, 3-trifluoromethylphenyl, 4-trifluoromethylphenyl, 4-ethoxyphenyl, 3-methylthiophenyl, 4-methylthiophenyl, 2fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 4-iodophenyl, and 4-methylthio-3-chlorophenyl.

By combination of the above described groups different antimicrobial compounds can be prepared. The preferred compounds are those exhibiting the greatest antimicrobial activity and which are adsorbed to the surface of teeth. Preferred compounds are those having the formula:

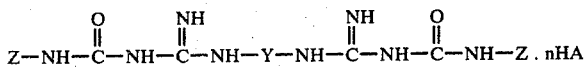

wherein Y is selected from the group consisting of pentamethylene, hexamethylene, heptamethylene, 1,4-cyclohexylenedimethyl, and α,α'-m-xylylene radicals and Z is selected from the group consisting of 2-ethylhexyl, 1,5-dimethylhexyl, 1,3-dimethylhexyl, 1,4-dimethylpentyl, cyclohexylmethyl, phenyl, 3-trifluoromethylphenyl, 4-trifluoromethylphenyl, 4-ethoxyphenyl, 3-methylthiophenyl, 4-methylthiophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 4-iodophenyl, and 4-methylthio-3-chlorophenyl radicals.

It should be understood that the term diloweralkylamino-substituted phenyl includes both compounds wherein the alkyl groups are separate and compounds in which the two alkyl groups attached to the amino nitrogen atom are part of a homocyclic or heterocyclic ring.

It is well known in the pharmacological arts that acid addition salts of pharmacologically active amine compounds do not differ in activities from their free bases. The salts merely provide a convenient solubility factor.

The carbamylguanidino compounds of this invention may be converted to their pharmaceutically acceptable acid addition salts by customary methods in the art. The pharmaceutically acceptable salts of this invention are those salts, the acid component of which is pharmacologically acceptable in the intended dosages. Suitable salts are those prepared from inorganic acids or organic acids. Such acids include: hydrochloric acid, hydrobromic acid, hydrofluoric acid, nitric acid, sulfuric acid, sulfamic acid, the polyphosphoric acids, phosphoric acid, monofluorophosphoric acid, glycerophosphoric acid, acetic acid, propionic acid, butyric acid, succinic acid, glycolic acid, 2,3-dihydroxypropionic acid, saccharic acid, gluconic acid, lactobionic acid, phenylacetic acid, cyclohexylcarboxylic acid, maleic acid, fumaric acid, lactic acid, citric acid, malic acid, camphoric acid, benzoic acid, salicyclic acid, phthalic acid, methanesulfonic acid, ethanesulfonic acid, benzenesulfonic acid, toluenesulfonic acid, nicotinic acid, and the like. Preferred acids are hydrochloric, acetic and gluconic.

Compounds containing the carbamylguanidino or thiocarbamylguanidino group can be prepared by the general reaction of an organic isocyanate or isothiocyanate with a substituted guanidine according to the following general reaction scheme:

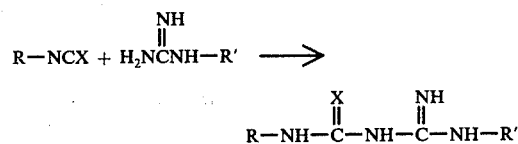

wherein R and R' represent organic radicals and X represents oxygen or sulfur.

The procedure for carrying out this reaction is described in Curd, J. Chem. Soc., 1949, 1732–1738.

To prepare a bis-carbamylguanidino compound according to this invention of the type:

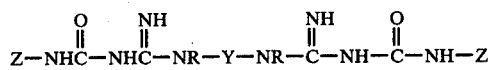

one mole of a bis-guanidino compound of the formula:

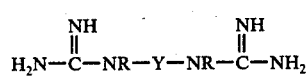

is reacted with two moles of an isocyanate having the formula:

Z—NCO by the procedure specified above. The corresponding compound having sulfur in place of oxygen, i.e., a compound having the formula:

is prepared analogously by reacting two moles of an isothiocyanate of the formula Z—NCS with one mole of a bis-guanidino compound. The isothiocyanate can be prepared from the corresponding isocyanate by reaction with O, O'-diethyldithiophosphate according to the process disclosed in U.S. Pat. No. 3,409,656.

When a compound of the formula:

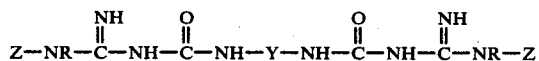

is to be prepared, one mole of a suitable diisocyanate of the formula

OCN—Y—NCO is reacted with two moles of a guanidine of the formula:

under the conditions specified above. Likewise, the analogous compound containing sulfur in place of oxygen, i.e. having the formula:

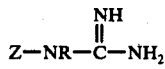

can be prepared by the same procedure using a diisothiocyanate in place of the diisocyanate.

Since both guanidines and isocyanates can be easily prepared from the corresponding amino compounds, the novel compounds of this invention may be synthesized from suitable readily available amines. Amino groups can be converted to isocyanate groups by reaction with phosgene, $COCl_2$. A particular synthesis for the preparation of diisocyanates by this reaction is given in British Pat. No. 901,337.

The guanidines or bis-guanidines required for synthesizing the compounds of this invention may be prepared from the corresponding amines by the well-known reaction with sodium cyanamide or by reaction with S-methylisothiourea sulfate according to the process described in Heyn, U.S. Pat. No. 1,737,192.

Thus the synthesis of compounds of either the formula:

or the formula:

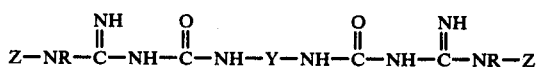

from readily available amines and diamines can be illustrated by the following scheme:

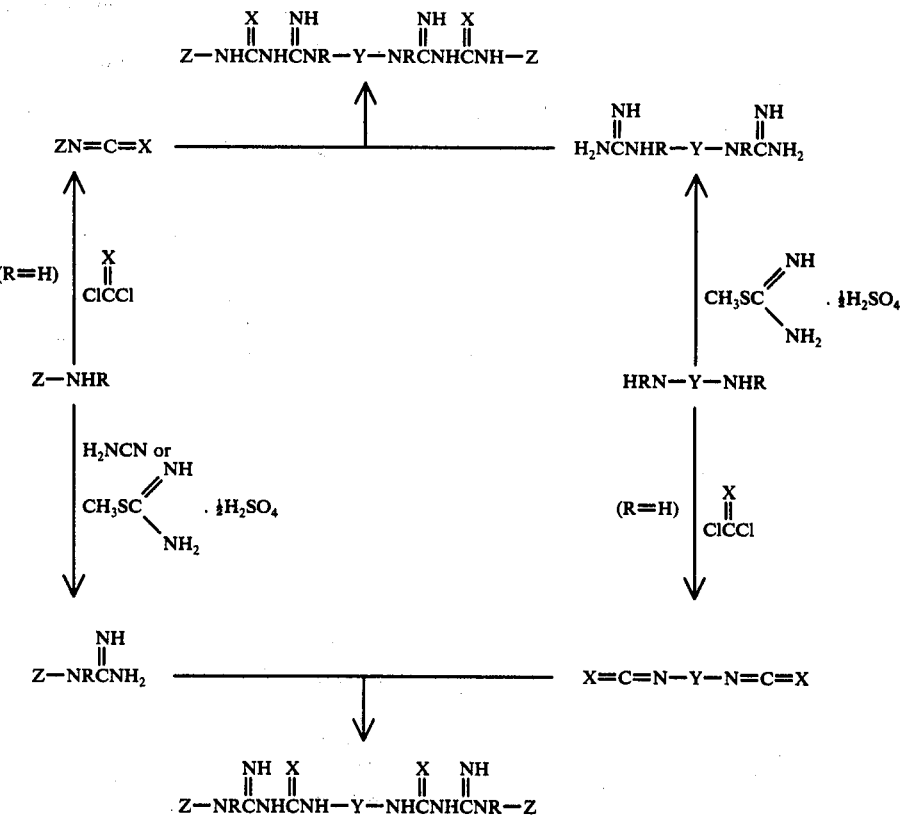

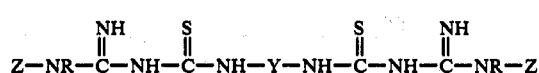

The reaction of substituted cyanoureas with diamines can also be used to prepare compounds of this invention of the formula:

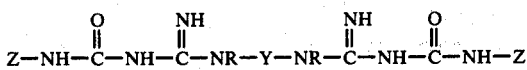

Thus if two moles of a substituted cyanourea of the formula:

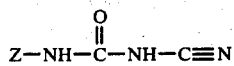

are reacted with one mole of a diamine dihydrochloride of the formula:

compounds of the above-described type can be obtained.

It will be understood by the skilled practitioner that compounds having substituents containing active hydrogen atoms, i.e., hydrogens reactive with isocyanates or isothiocyanates, cannot be used in the direct reaction of the guanidino compound with the isocyanate according to the above scheme. In order to obtain bis-carbamylguanidino compounds having groups containing active hydrogen an active hydrogen site in the precursor reagent must be blocked by a group not containing active hydrogen. The blocking group can be removed after the reaction between the guanidine and the isocyanate has been completed.

For example, a compound of this invention containing a carboxyl group in the Z portion of the molecule can be prepared by using a reagent containing an esterified carboxyl group in the Z portion of the reagent. After the reaction between the guanidino compound and the isocyanate has taken place, the ester group may be hydrolyzed by techniques well known to those skilled in the art to yield a bis(carbamylguanidino) compound containing a carboxyl group. In similar fashion, reagents containing amino groups blocked by the formation of a Schiff base or amide, and hydroxyl groups blocked by acylation can be used to form bis(carbamylguanidino) compounds according to the invention. The blocking groups subsequently can be removed by well-known techniques to produce compounds containing amino or hydroxyl groups.

Likewise, further chemical conversions can be performed on substituent groups present in the Z portion of the compounds of this invention. For example, nitro groups can be reduced to amino groups by known techniques. The amino groups so formed can be converted to amido groups by reaction with an acid anhydride, converted to phenols by diazotization followed by reaction with water or converted to mercaptans by successive reaction with potassium xanthate and water. The phenols can be further converted to the acyl derivative by reaction with a carboxylic acid anhydride or acid chloride. The nitro groups can also be converted to secondary amino groups by reduction in the presence of an aldehyde.

Ester groups can be converted into amides or substituted amides by reaction with ammonia or primary or secondary amines.

By reacting compounds containing alkylthio groups with chlorine water, the alkylthio groups can be converted into sulfonyl chloride groups. These can be further converted into sulfonic acid groups by hydrolysis or sulfonamido groups by reaction with ammonia, primary amines or secondary amines. Alkylthio groups can also be oxidized by known techniques to yield alkylsulfinyl and alkylsulfonyl groups.

The acid addition salts of the novel compounds are prepared by adding a solution containing an equivalent amount of the corresponding acid to a solution of the compound.

The equivalent amount is determined by the number of ionizable hydrogen atoms present in the acid, and the salt that is desired. The novel compounds of this invention contain two basic sites in the molecule one or both of which may react with the ionizable hydrogen atoms of the acid. Thus, one or two moles of a monobasic acid such as hydrochloric acid, acetic acid, or gluconic acid may react with one mole of the novel compound to form the mono or di-salt respectively. Likewise, one-half or one mole of a dibasic acid such as sulfuric acid or succinic acid may react with one mole of the bis-carbamylguanidine. Again, a tribasic acid such as phosphoric acid or citric acid, may combine in proportions of ⅓, ⅔, ⅔, 1, or 2 moles of acid to one mole of bis-carbamylguanidine.

The compounds of this invention can, in certain instances, possess one or more asymmetric carbon atoms and consequently can be obtained as racemic mixtures or as dextro (+) and levorotatory (−) isomers. These may be separated by any of the known methods of resolution. A method that may be employed is combining the racemic compound with an optically active acid, for example by salt formation. Two products are then obtained. If the compounds of this invention are added to an optically active acid such as (+) or (−) tartaric acid, then the salts produced possess different properties and different solubilities and can be separated by fractional crystallization. When the salts have been separated by repeated crystallization, the acid is split off and the pure (+) or (−) isomer is obtained. It is to be understood that these optical isomers are embraced within the extent of this invention.

Adsorption of the compounds of this invention to extracted, non-carious, unprepared enamel tooth surfaces was investigated by the following procedure. Extracted human teeth, having their roots coated with wax so that only the enamel crowns were exposed, were immersed in 10 ml portions of stirred agueous solutions of the test compound having a concentration of 10 micrograms/milliliter. After 10 minutes, the teeth were removed and the amount of test compound removed from the solution by adsorption was determined spectrophotometrically. The teeth were reimmersed for successive 10 minute periods until no further adsorption occurred. The adsorption of the compounds of this invention was compared with that of chlorohexidine and found to be substantially greater. In one experiment, the adsorption of 1,6-bis(4-chlorophenylcarbamylguanidino)hexane diacetate was found to be about twice as great as that of chlorhexidine acetate over a period of about ten minutes. After no more of the test compounds was removed from the solution by adsorption, the teeth were immersed in fresh portions of the solutions. No further adsorption of chlorhexidine occurred, while the compound of this invention continued to be adsorbed to the tooth surface. From a total of four successive fresh portion of solution over a period of about 4 hours, about seven times as much of the 1,6-bis(4-chlorophenylcarbamylguanidino)hexane was adsorbed as of the chlorhexidine.

The antimicrobial activity of the compounds of the invention is determined by the following in vitro assays:

A zone of inhibition test is performed by placing a ¼" diameter filter paper disk wet with an aqueous solution of the test compound of the chosen concentration on a brain-heart infusion or trypticase soy agar plate seeded with the microorganism to be inhibited. The plate is incubated at 37° C. for 24 hrs. and the diameter of the zone around the filter paper in which growth of the microorganism has been inhibited is measured. The greater the diameter of the zone of inhibition, the more effective is the compound against the particular microorganism. This test may also be run with the medium diluted with an equal volume of water.

A quantitative serial dilution test may also be performed by the following procedure.

A 20mg/ml solution of the compound to be tested is prepared in a standard brain-heart infusion broth medium which has been diluted with water to one-half standard strength. Serial dilutions are prepared by adding 1 ml of the solution to a test tube containing 9ml of medium. Five milliliters of the resulting solution are then added to another test tube containing 5ml of the medium. The resulting solution is then again diluted by the same procedure. Ordinarily one tenfold dilution and four twofold dilutions are made. The procedure can be continued if more dilute solutions are required. Each of the series of tubes containing solutions of the compounds to be assayed is inoculated with two drops of a heavy culture of the chosen microorganisms in the brain-heart infusion broth. The tubes are incubated at 37° C. for 36 hours and the most dilute solution showing no microbial growth is noted. The concentration of this solution is reported as the minimal inhibitory concentration (MIC).

When tested by these procedures, the compounds of this invention show antimicrobial activity at some concentration against the microorganisms *Streptococcus mutans, Actinomyces viscosus,* and *Actinomyces naeslundi, Staph. aureus, E. Coli, Ps. aeruginosa* and *C. albicans.*

The potency of antimicrobial activity of the compounds of this invention varies considerably according to the nature of Z, B, and Y. Among the compounds with higher potency are those in which Z is phenyl, halophenyl, trifluoromethylphenyl, and 2-ethylhexyl, and Y is pentamethylene, hexamethylene, or heptamethylene and B is carbamylguanidino.

Acute oral toxicity of the compounds of this invention is determined in mice by the following procedure. The mice are fasted overnight, then formed into groups of 10 for testing. The animals in each group are fed a chosen dose and the dose is varied from group to group to cover a range of doses. The groups are then observed for a period of 5 days and the number of dead animals in each group is noted each day. The $LD_{50}$ is calculated from this data according to the method of Weil, *Biometrics,* 8(3), 249 263 (1952).

The compounds of this invention show a very low order of acute oral toxicity, e.g., 1,6-bis(4-chlorophenylcarbamylguanidino)hexane is essentially atoxic in mice at 8 gms/Kg orally.

The taste of compounds of this invention may be evaluated by standard taste panels. The compounds of this invention are devoid of the bitter taste associated with chlorhexidine and in many cases, e.g., aqueous solutions of 1,6-bis(4-chlorophenylcarbamylguanidino)- hexane digluconate, are essentially tasteless at the concentration useful for microbial inhibition.

The novel compounds of this invention are useful as topical antimicrobial agents. Suitable solution concentrations of these compounds for topical application to exert their antimicrobial activities are in the range of 0.005% to 10%, preferably 0.05% to 2%.

The invention will be further illustrated by the following examples which are not, however, intended to limit its scope.

EXAMPLE I

1,6-Bis-(p-chlorophenylcarbamylguanidino)hexane

Sodium (5g.0.22 g-at) is dissolved in 250ml of dry acetone with cooling and under a nitrogen atmosphere. 1,6-Bis(guanidino)hexane sulfate (30g.0.1m) is added and the mixture is stirred at room temperature for 2 hours. A solution of 30g (0.2m) of p-chlorophenylisocyanate in dry acetone is added and the mixture is stirred at room temperature for 4 hours, and at reflux temperature for 4 hours. The reaction mixture is concentrated to ½ its volume and poured into 5 volumes of water, whereupon the crude product precipitates. The solvent is decanted and the residue is triturated with diethyl ether. The slurry is filtered and the base collected as a white granular precipitate, which is recrystallized from acetone. M.P. 151°–153° C. Analysis: Calculated: C=52.07, H=5.52, Cl=14.00, N=22.09. Found: C=52.23, H=5.75, Cl=14.03, N=21.88.

The diacetate of this compound is prepared by dissolving 5g of the free base prepared above in 25ml of glacial acetic acid by heating at about 90° C. The solution is cooled and the white precipitated diacetate collected on a filter. The diacetate is triturated with ether, and is collected on a filter. M.P. 174°–176° C. An aqueous solution of the digluconate salt of this compound is prepared by suspending 1.89g (0.0037m) of the free base prepared above in 10ml of a 50% aqueous solution of gluconic acid and warming the suspension while adding water until a total volume of 200ml is attained.

The hydrochloride of this compound is prepared by suspending 2.6 gm of the free base prepared above in 50ml of water containing 10ml 36% hydrochloric acid and stirring with warming for 1 hour, then collecting the product on a filter. M.P. 208°–212° C.

EXAMPLE II

1,6-Bis(p-chlorophenylamidinoureido)hexane.

Sodium 1 gm. (0.04g-at) is dissolved in 100ml of acetone. p-Chlorophenylguanidine carbonate 8 gm. (0.02m) is added and stirred for ½ hr. 1,6-Hexamethylene diisocyanate dissolved in 20ml of acetone, is added dropwise to the first solution and stirred for 2 hours at room temperature, two hours at reflux temperature and allowed to stand for 16 hours. The precipitated product is collected on a filter, washed with acetone and washed with water. M.P. 186°–190° C. Analysis: Calculated: C=52.07, H=5.52, Cl=14.00, N=22.09. Found: C=52.48, H=5.71, Cl=12.99, N=21.73

EXAMPLE III

By the procedure of Example I the following compounds are prepared by reacting the isocyanate given in Column 1 of Table I with the bis-guanidine given in Column 2 to yield the novel compound listed in Column 3.

TABLE I

| ISOCYANATE | BIS-GUANIDINE | COMPOUNDS |
|---|---|---|
| 4-chlorophenyl isocyanate | 1,5-bis(guanidino)pentane | 1,5-bis(4-chlorophenylcarbamyl-guanidino)pentane acetate (M.P. 140°–142° C |
| 4-chlorophenyl isocyanate | 1,7-bis(guanidino)heptane | 1,7-bis(4-chlorophenylcarbamyl-guanidino)heptane dihydrochloride (M.P. 170°–175° C dec.) |
| 2-chlorophenyl isocyanate | 1,6-bis(guanidino)hexane | 1,6-bis(2-chlorophenylcarbamyl-guanidino)hexane diacetate (M.P. 138.5°–142° C dec.) |
| 3-trifluoromethylphenyl isocyanate | 1,6-bis(guanidino)hexane | 1,6-bis(3-trifluoromethylphenyl-carbamylguanidino)hexane dihydrochloride (M.P. 138°–140° C) |
| 3-chlorophenyl isocyanate | 1,1-bis(guanidino)hexane | 1,6-bis(3-chlorophenylcarbamyl-guanidino)hexane diacetate (M.P. 157°–159° C dec.) |
| 2-ethylhexyl isocyanate | 1,6-bis(guanidino)hexane | 1,6-bis(2-ethylhexylcarbamyl-guanidino)hexane (M.P. 98°–101° C) |
| 4-nitrophenyl isocyanate | 1,6-bis(guanidino)hexane | 1,6-bis(4-nitrophenylcarbamyl-guanidino)hexane diacetate (M.P. 175°–179° C dec.) |
| phenyl isocyanate | 1,6-bis(guanidino)hexane | 1,6-bis(phenylcarbamylguanidino)-hexane diacetate (M.P. 151°–155° C) |
| 4-bromophenyl isocyanate | 1,6-bis(guanidino)hexane | 1,6-bis(4-bromophenylcarbamyl-guanidino)hexane diacetate (M.P. 180°–185° C dec.) |
| 4-fluorophenyl isocyanate | 1,6-bis(guanidino)hexane | 1,6-bis(4-fluorophenylcarbamyl-guanidino)hexane diacetate (M.P. 175°–178° C) |
| methyl isocyanate | 1,6-bis(guanidino)hexane | 1,6-bis(methylcarbamylguanidino)-hexane trihydrate (M.P. 115°–119° C dec.) |

EXAMPLE IV 1,6-Bis(p-chlorophenylthiocarbamylguanidino)hexane diacetate

Sodium (0.05g, 0.02m) is dissolved in dry acetone and 3.0 grams (0.01m) of 1,6-bis(guanidino)hexane sulfate is added. The resulting suspension is stirred for two hours at room temperature and thereafter 3.4 grams (0.02m) of 4-chlorophenyl isothiocyanate is added. The mixture is heated at 60° for 3 hours, then stirred overnight at room temperature. Ten milliliters of methanol are added to decompose residual sodium. The solvent is distilled and the residue is washed by decantation with several portions of water to leave the product as the free base. The residue is dissolved in 60ml. of warm acetic acid. The solution is cooled and the diacetate which precipitates is collected on a filter, washed with acetic acid, then recrystallized from acetic acid, M.P. 145°–148° C.

Analysis: Calculated: C=47.20, H=5.79, N=16.74, S=9.69, Cl=10.72. Found: C=47.12, H=5.23, N=17.16, S=10.11, Cl=11.00.

EXAMPLE V

When the procedures of Example I are followed using the reagents listed in Table II, the corresponding compounds listed in Table II are prepared.

Likewise, by the procedures of Example II, using the reagents listed in Table III, the corresponding compounds listed in Table III are prepared.

TABLE II

| REAGENTS | | |
|---|---|---|
| Isocyanate | Bis-guanidine | COMPOUNDS |
| 4-chlorophenyl isocyanate | 1,2-bis(guanidino)ethane | 1,2-bis(4-chlorophenylcarbamyl-guanidino)ethane |
| 4-chlorophenyl isocyanate | 1,3-bis(guanidino)propane | 1,3-bis(4-chlorophenylcarbamyl-guanidino)propane |
| 4-chlorophenyl isocyanate | 1,4-bis(guanidino)butane | 1,4-bis(4-chlorophenylcarbamyl-guanidino)butane |
| 4-chlorophenyl isocyanate | 1,8-bis(guanidino)octane | 1,8-bis(4-chlorophenyl carbamyl-guanidino)octane |
| 4-chlorophenyl isocyanate | 1,9-bis(guanidino)nonane | 1,9-bis(4-chlorophenylcarbamyl-guanidino)nonane |
| 4-chlorophenyl isocyanate | 1,10-bis(guanidino)decane | 1,10-bis(4-chlorophenylcarbamyl-guanidino)decane |
| 4-chlorophenyl isocyanate | 1,11-bis(guanidino)undecane | 1,11-bis(4-chlorophenylcarbamyl-guanidino)undecane |
| 4-chlorophenyl isocyanate | 1,12-bis(guanidino)dodecane | 1,12-bis(4-chlorophenylcarbamyl-guanidino)dodecane |
| 4-chlorophenyl isocyanate | 1,4-bis(guanidino)-2-butene | 1,4-bis(4-chlorophenylcarbamyl-guanidino)-2-butene |
| 4-chlorophenyl isocyanate | 1,3-bis(guanidino)cyclohexane | 1,3-bis(4-chlorophenylcarbamyl-guanidino)cyclohexane |
| 4-chlorophenyl isocyanate | 1,4-bis(guanidinomethyl)-cyclohexane | 1,4-bis(4-chlorophenylcarbamyl-guanidinomethyl)cyclohexane |
| 4-chlorophenyl isocyanate | 1,4-bis(guanidino)benzene | 1,4-bis(4-chlorophenylcarbamyl-guanidino)benzene |
| 4-chlorophenyl isocyanate | 2,4-bis(guanidino)toluene | 2,4-bis(4-chlorophenylcarbamyl-guanidino)toluene |
| 4-chlorophenyl isocyanate | α,α'-bis(guanidino)-m-xylene | α,α'-bis(4-chlorophenylcarbamyl-guanidino)-m-xylene |
| 4-chlorophenyl isocyanate | α,3-bis(guanidino)toluene | α,3-bis(4-chlorophenylcarbamyl-guanidino)toluene |
| hexyl isocyanate | 1,6-bis(guanidino)hexane | 1,6-bis(hexylcarbamylguanidino)-hexane |
| dodecyl isocyanate | 1,6-bis(guanidino)hexane | 1,6-bis(dodecylcarbamylguanidino)- |

TABLE II-continued

| REAGENTS | | |
|---|---|---|
| Isocyanate | Bis-guanidine | COMPOUNDS |
| 1-methylhexyl isocyanate | 1,6-bis(guanidino)hexane | 1,6-bis(1-methylhexylcarbamylguanidino)hexane |
| 1,3-dimethylpentyl isocyanate | 1,6-bis(guanidino)hexane | 1,6-bis(1,3-dimethylpentylcarbamylguanidino)hexane |
| 1,4-dimethylpentyl isocyanate | 1,6-bis(guanidino)hexane | 1,6-bis(1,4-dimethylpentylcarbamylguanidino)hexane |
| 1,5-dimethylhexyl isocyanate | 1,6-bis(guanidino)hexane | 1,6-bis(1,5-dimethylhexylcarbamylguanidino)hexane |
| allyl isocyanate | 1,6-bis(guanidino)hexane | 1,6-bis(allylcarbamylguanidino)hexane |
| 2-ethyl-2-hexenyl isocyanate | 1,6-bis(guanidino)hexane | 1,6-bis(2-ethyl-2-hexenylcarbamylguanidino)hexane |
| 9-decenyl isocyanate | 1,6-bis(guanidino)hexane | 1,6-bis(9-decenylcarbamylguanidino)hexane |
| 3-butynyl isocyanate | 1,6-bis(guanidino)hexane | 1,6-bis(3-butynylcarbamylguanidino)hexane |
| cyclohexyl isocyanate | 1,6-bis(guanidino)hexane | 1,6-bis(cyclohexylcarbamylguanidino)hexane |
| 1-adamantyl isocyanate | 1,6-bis(guanidino)hexane | 1,6-bis(1-adamantylcarbamylguanidino)hexane |
| cyclohexylmethyl isocyanate | 1,6-bis(guanidino)hexane | 1,6-bis(cyclohexylmethylcarbamylguanidino)hexane |
| cycloheptylmethyl isocyanate | 1,6-bis(guanidino)hexane | 1,6-bis(cycloheptylmethylcarbamylguanidino)hexane |
| 1-naphthyl isocyanate | 1,6-bis(guanidino)hexane | 1,6-bis(1-naphthylcarbamylguanidino)hexane |
| benzyl isocyanate | 1,6-bis(guanidino)hexane | 1,6-bis(benzylcarbamylguanidino)hexane |
| 2-phenylcyclopropyl isocyanate | 1,6-bis(guanidino)hexane | 1,6-bis(2-phenylcyclopropylcarbamylguanidino)hexane |
| 4-tolyl isocyanate | 1,6-bis(guanidino)hexane | 1,6-bis(4-tolylcarbamylguanidino)hexane |
| 4-hexylphenyl isocyanate | 1,6-bis(guanidino)hexane | 1,6-bis(4-hexylphenylcarbamylguanidino)hexane |
| 2,6-diethylphenyl isocyanate | 1,6-bis(guanidino)hexane | 1,6-bis(2,6-diethylphenylcarbamylguanidino)hexane |
| 4-trifluoromethylphenyl isocyanate | 1,6-bis(guanidino)hexane | 1,6-bis(4-trifluoromethylphenylcarbamylguanidino)hexane |
| 2-trifluoromethylphenyl isocyanate | 1,6-bis(guanidino)hexane | 1,6-bis(2-trifluoromethylphenylcarbamylguanidino)hexane |
| 3-trifluoromethylbenzyl isocyanate | 1,6-bis(guanidino)hexane | 1,6-bis(3-trifluoromethylbenzylcarbamylguanidino)hexane |
| 4-butoxyphenyl isocyanate | 1,6-bis(guanidino)hexane | 1,6-bis(4-butoxyphenylcarbamylguanidino)hexane |
| 4-trifluoromethoxyphenyl isocyanate | 1,6-bis(guanidino)hexane | 1,6-bis(4-trifluoromethoxyphenylcarbamylguanidino)hexane |
| 4-phenoxyphenyl isocyanate | 1,6-bis(guanidino)hexane | 1,6-bis(4-phenoxyphenylcarbamylguanidino)hexane |
| 4-methylthiophenyl isocyanate | 1,6-bis(guanidino)hexane | 1,6-bis(4-methylthiophenylcarbamylguanidino)hexane |
| 2-fluorophenyl isocyanate | 1,6-bis(guanidino)hexane | 1,6-bis(2-fluorophenylcarbamylguanidino)hexane |
| 3-fluorophenyl isocyanate | 1,6-bis(guanidino)hexane | 1,6-bis(3-fluorophenylcarbamylguanidino)hexane |
| 3-bromophenyl isocyanate | 1,6-bis(guanidino)hexane | 1,6-bis(3-bromophenylcarbamylguanidino)hexane |
| 4-iodophenyl isocyanate | 1,6-bis(guanidino)hexane | 1,6-bis(4-iodophenylcarbamylguanidino)hexane |
| 4-chlorobenzyl isocyanate | 1,6-bis(guanidino)hexane | 1,6-bis(4-chlorobenzylcarbamylguanidino)hexane |
| 4-acetylphenyl isocyanate | 1,6-bis(guanidino)hexane | 1,6-bis(4-acetylphenylcarbamylguanidino)hexane |
| 2,4-dichlorophenyl isocyanate | 1,6-bis(guanidino)hexane | 1,6-bis(2,4-dichlorophenylcarbamylguanidino)hexane |
| 4-dimethylaminophenyl isocyanate | 1,6-bis(guanidino)hexane | 1,6-bis(4-dimethylaminophenylcarbamylguanidino)hexane |
| 4-butylsulfonylphenyl isocyanate | 1,6-bis(guanidino)hexane | 1,6-bis(4-butylsulfonylphenylcarbamylguanidino)hexane |
| 3-fluorosulfonylphenyl isocyanate | 1,6-bis(guanidino)hexane | 1,6-bis(3-fluorosulfonylphenylcarbamylguanidino)hexane |
| 4-chloro-3-trifluoromethyl isocyanate | 1,6-bis(guanidino)hexane | 1,6-bis(4-chloro-3-trifluoromethylcarbamylguanidino)hexane |
| 3-chloro-4-fluorophenyl isocyanate | 1,6-bis(guanidino)hexane | 1,6-bis(3-chloro-4-fluorophenylcarbamylguanidino)hexane |
| 4-methylthio-3-chlorophenyl isocyanate | 1,6-bis(guanidino)hexane | 1,6-bis(4-methylthio-3-chlorophenylcarbamylguanidino)hexane |
| heptyl isothiocyanate | 1,6-bis(guanidino)hexane | 1,6-bis(heptylthiocarbamylguanidino)hexane |
| 4-ethoxycarbonylphenyl isocyanate | 1,6-bis(guanidino)hexane | 1,6-bis(4-ethoxycarbonylphenylcarbamylguanidino)hexane |
| 4-chlorophenyl isocyanate | 1,6-bis(1-methylguanidino)hexane | 1,6-bis[1-(p-chlorophenylcarbamyl)-3-methyl-3-guanidino]hexane |
| benzyl isothiocyanate | 1,6-bis(guanidino)hexane | 1,6-bis(benzylthiocarbamylguanidino)hexane |
| 4-fluorophenyl isothiocyanate | 1,6-bis(guanidino)hexane | 1,6-bis(4-fluorophenylthiocarbamylguanidino)hexane |
| 4-chlorophenyl isothiocyanate | 1,6-bis(guanidino)hexane | 1,6-bis(4-chlorophenylthiocarbamylguanidino)hexane |
| 3-trifluoromethylphenyl isothiocyanate | 1,6-bis(guanidino)hexane | 1,6-bis(3-trifluoromethylphenylthiocarbamylguanidino)hexane |

TABLE II-continued

| REAGENTS | | COMPOUNDS |
|---|---|---|
| Isocyanate | Bis-guanidine | |
| 4-cyanophenyl isothiocyanate | 1,6-bis(guanidino)hexane | 1,6-bis(4-cyanophenylthiocarbamyl-guanidino)hexane |

TABLE III

| REAGENTS | | COMPOUNDS |
|---|---|---|
| Guanidine | Diisocyanate | |
| 1-(2-ethylhexyl)guanidine | 1,6-hexamethylene diisocyanate | 1,6-bis(2-ethylhexylamidinoureido)-hexane |
| 1-(4-chlorophenyl)guanidine | 1,6-hexamethylene diisothiocyanate | 1,6-bis(4-chlorophenylamidino-thioureido)hexane |
| 1-(2-ethylhexyl)guanidine | 1,6-hexamethylene diisothiocyanate | 1,6-bis(2-ethylhexylamidinothio-ureido)hexane |

EXAMPLE VI

The minimum inhibitory concentration of a number of the compounds of this invention with respect to the microorganism S. Mutans were determined by the procedure described above. The results are tabulated in Table III. Chlorhexidine diacetate a commercially successful antimicrobial was used as a control.

TABLE III

| Compound | MIC (micrograms/ml) |
|---|---|
| 1,6-bis(4-chlorophenylcarbamyl-guanidino)hexane diacetate | 0.078 |
| 1,6-bis(3-trifluoromethylphenylcarbamyl-guanidino)hexane dihydrochloride | 0.312 |
| 1,6-bis(3-chlorophenylcarbamylguanidino)hexane diacetate | 0.078 |
| 1,6-bis(2-chlorophenylcarbamylguanidino)-hexane diacetate | 0.312 |
| 1,5-bis(4-chlorophenylcarbamylguanidino)-pentane monoacetate | 0.078 |
| 1,7-bis(4-chlorophenylcarbamylguanidino)-heptane dihydrochloride | 0.312 |
| 1,6-bis(4-bromophenylcarbamylguanidino)-hexane diacetate | 0.312 |
| 1,6-bis(2-ethylhexylcarbamylguanidino)-hexane | 0.625 |
| 1,6-bis(phenylcarbamylguanidino)hexane | 0.625 |
| 1,6-bis(4-fluorophenylcarbamylguanidino)-hexane diacetate | 0.156 |
| 1,6-bis(4-chlorophenylamidinoureido)hexane | 2.55 |
| 1,4-bis(4-chlorophenylcarbamylguanidino)butane | 0.625 |
| chlorhexidine diacetate | 0.078 |

It can be seen from these results that the compounds of this invention are comparable in antimicrobial effect to the presently used antimicrobial chlorhexidine.

I claim:

1. A compound having the formula Z—B—Y—B'—Z .nHA wherein Y is a bivalent organic radical selected from the group consisting of $C_2$-$C_{12}$ alkylene, $C_5$-$C_{12}$ cycloalkylene, $C_5$-$C_{12}$ cycloalkylenebis(loweralkyl), $C_6$-$C_{12}$ arylene and loweralkylarylene, $C_7$-$C_{12}$ aryleneloweralkyl, and $C_8$-$C_{12}$ arylenebis(loweralkyl); B is a carbamylguanidino group; B' is B; and Z is selected from the group consisting of $C_1$-$C_{12}$ alkyl; $C_3$-$C_{12}$ alkenyl; $C_3$-$C_{12}$ alkynyl; $C_3$-$C_{12}$ cycloalkyl, $C_4$-$C_{12}$ cycloalkylalkyl; and pharmacologically acceptable addition salts of these compounds with acids represented by nHA wherein $n=0$, ⅓, ½, ⅔, 1, and 2 and HA is an inorganic or organic acid.

2. A compound according to claim 1 wherein Y is selected from the group consisting of $C_4$-$C_8$ alkylene, $C_5$-$C_8$ cycloalkylene, $C_5$-$C_8$ cycloalkylenebis(loweralkyl), $C_6$-$C_8$ arylene and loweralkylarylene, $C_7$-$C_8$ aryleneloweralkyl, and $C_8$ arylenebis(loweralkyl) radicals.

3. A compound according to claim 1 wherein Z is selected from the group consisting of $C_4$-$C_{10}$ alkyl, $C_5$-$C_9$ cycloalkyl, and $C_6$-$C_9$ cycloalkylalkyl radicals.

4. A compound according to claim 1 having the formula:

5. A compound according to claim 1 having the formula:

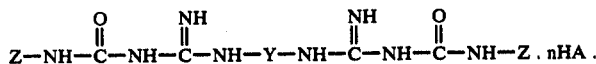

6. A compound according to claim 5 wherein Y is selected from the group consisting of $C_4$-$C_8$ alkylene, $C_5$-$C_8$ cycloalkylene, $C_5$-$C_8$ cycloalkylenebis(loweralkyl), $C_6$-$C_8$ arylene and loweralkylarylene, $C_7$-$C_8$ aryleneloweralkyl, and $C_8$ arylenebis(loweralkyl) radicals.

7. A compound according to claim 5 wherein Z is selected from the group consisting of $C_4$-$C_{10}$ alkyl, $C_5$-$C_9$ cycloalkyl, and $C_6$-$C_9$ cycloalkylalkyl radicals.

8. A compound according to claim 5 wherein Y is selected from the group consisting of $C_4$-$C_8$ alkylene, $C_5$-$C_8$ cycloalkylene, $C_5$-$C_8$ cycloalkyenebis(loweralkyl), $C_6$-$C_8$ arylene and loweralkylarylene, $C_7$-$C_8$ aryleneloweralkyl, and $C_8$ arylenebis (loweralkyl) radicals, and Z is selected from the group consisting of $C_4$-$C_{10}$ alkyl, $C_5$-$C_9$ cycloalkyl, and $C_6$-$C_9$ cycloalkylalkyl radicals.

9. A compound according to claim 8 wherein Y is selected from the group consisting of pentamethylene, hexamethylene, heptamethylene, 1,4-cyclohexylenedimethyl, and α,α'-m-xylene radicals and Z is selected from the group consisting of 2-ethylhexyl, 1,3-dimethylpentyl, 1,4-dimethylpentyl, 1,5-dimethylhexyl, and cyclohexylmethyl radicals.

10. A compound according to claim 8 wherein Y is $C_5$-$C_7$ polymethylene and Z is 2-ethylhexyl.

11. A compound according to claim 1 wherein said acid, HA, is selected from the group consisting of hydrochloric acid, hydrobromic acid, nitric acid, sulfuric acid, acetic acid, glycolic acid, 2,3-dihydroxypropionic acid, saccharic acid, gluconic acid, lactobionic acid, maleic acid, fumaric acid, lactic acid, citric acid, malic acid, methanesulfonic acid, and ethanesulfonic acid.

12. 1,6-Bis(2-ethylhexylcarbamylguanidino)hexane and pharmacologically acceptable acid addition salts.

13. 1,6-Bis(1-adamantylcarbamylguanidino)hexane and pharmacologically acceptable acid addition salts.

14. 1,6-Bis(cyclohexylmethylcarbamylguanidino)-hexane and pharmacologically acceptable acid addition salts.

* * * * *

UNITED STATES PATENT OFFICE
CERTIFICATE OF CORRECTION

Patent No. 4,115,447  Dated September 19, 1978

Inventor(s) JULIUS DIAMOND

It is certified that error appears in the above-identified patent and that said Letters Patent are hereby corrected as shown below:

Column 3, line 12, "hydroxapatite" should read --hydroxyapatite--.
Column 4, lines 66-67, delete "dimethylaminophenyl."
Column 5, lines 6-7, delete "2-chloro-5-nitrophenyl."
Column 5, line 36, "2fluorophenyl" should read --2-fluorophenyl--.
Column 6, line 23, "salicyclic" should read --salicylic--.
Column 10, line 45, "agueous" should read --aqueous--.
Column 13, Table I, second column, fourth compound, "1,6-bis-(guanidino(hexane" should read --1,6-bis(guanidino)hexane--.
Column 17, lines 23 and 25, "III" should read --IV--.

Signed and Sealed this

Twenty-seventh Day of March 1979

[SEAL]

Attest:

RUTH C. MASON
Attesting Officer

DONALD W. BANNER
Commissioner of Patents and Trademarks